United States Patent [19]

Guerineau et al.

[11] Patent Number: 5,267,976
[45] Date of Patent: Dec. 7, 1993

[54] SYRINGE WITH SELF-RETRACTING NEEDLE

[75] Inventors: Jean Guerineau; Dominique Poirier, both of Issy-les-Moulineaux, France

[73] Assignee: Blue Star Corporation S.A.

[21] Appl. No.: 923,944

[22] PCT Filed: Jul. 27, 1990

[86] PCT No.: PCT/FR90/00572
§ 371 Date: Sep. 4, 1992
§ 102(e) Date: Sep. 4, 1992

[87] PCT Pub. No.: WO91/13643
PCT Pub. Date: Sep. 19, 1991

[30] Foreign Application Priority Data

Mar. 8, 1990 [FR] France .................. 90 02964

[51] Int. Cl.⁵ .............................. A61M 5/32
[52] U.S. Cl. ........................... 604/198; 604/263
[58] Field of Search ............ 604/198, 187, 192, 263

[56] References Cited

U.S. PATENT DOCUMENTS

| 4,664,654 | 5/1987 | Strauss | 604/198 |
| 4,813,940 | 3/1989 | Parry | 604/198 |
| 4,911,693 | 3/1990 | Paris | 604/192 |

FOREIGN PATENT DOCUMENTS

| 0288003 | 10/1988 | European Pat. Off. . |
| 0307367 | 3/1989 | European Pat. Off. . |
| 0405039 | 1/1991 | European Pat. Off. . |

Primary Examiner—John D. Yasko
Attorney, Agent, or Firm—Ostrolenk, Faber, Gerb & Soffen

[57] ABSTRACT

A syringe comprises a body (1) which carries the needle (6), a piston (13), a protective sheath and a spring (17) arranged between the sheath (14) and the body (1). A first and a second shoulder (21) on the outer wall of the body (1) co-operate with a first spur (19) of the sheath (14) to block the body (1) in a first direction, which a second, supple spur (20) and a third shoulder (24) block the body (1) in the other direction.

14 Claims, 2 Drawing Sheets

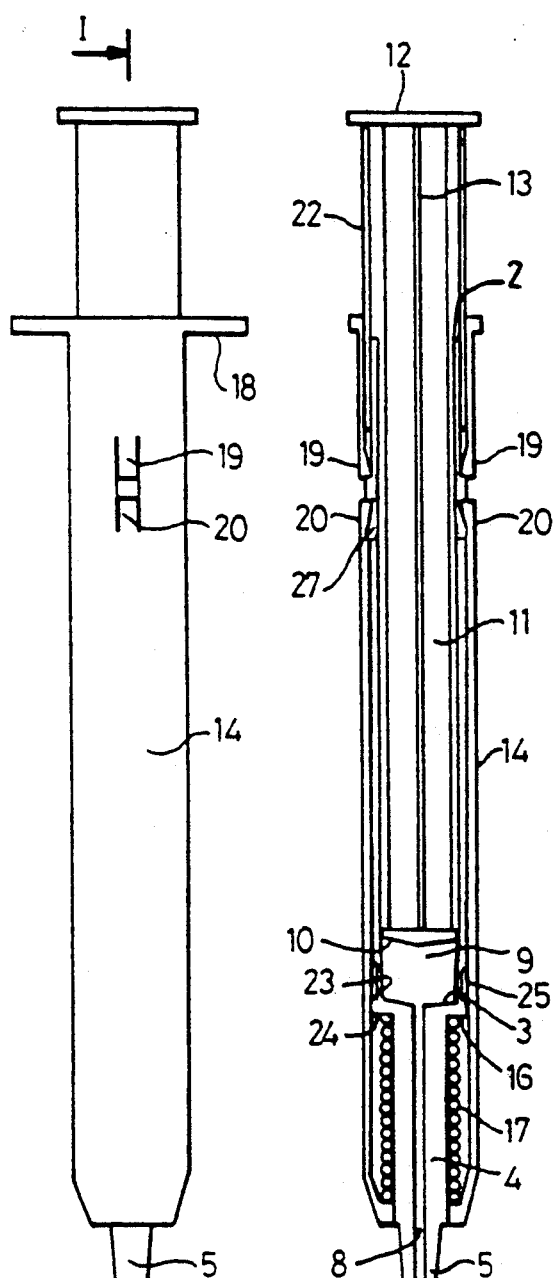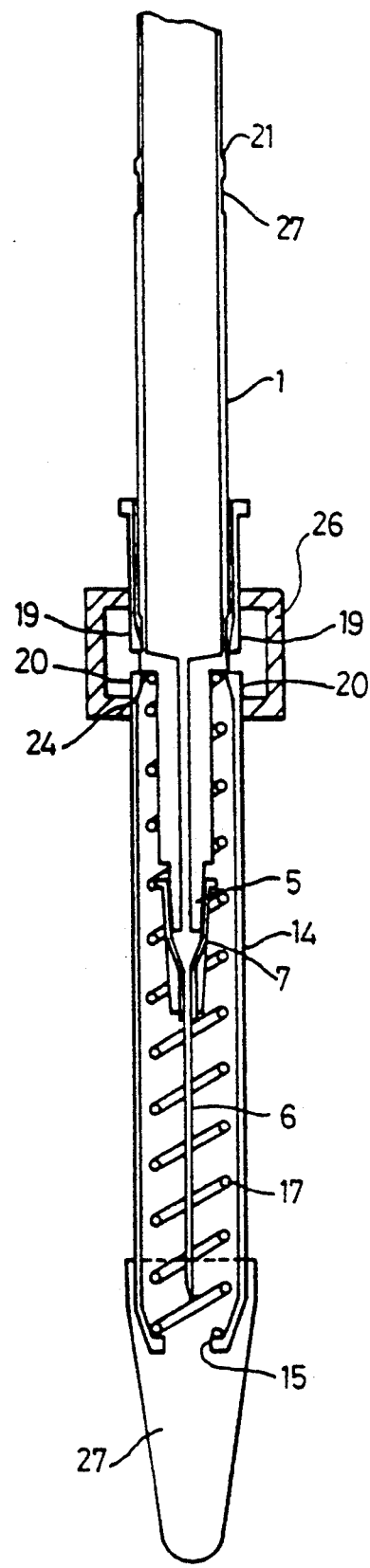
FIG.1  FIG.2  FIG.3

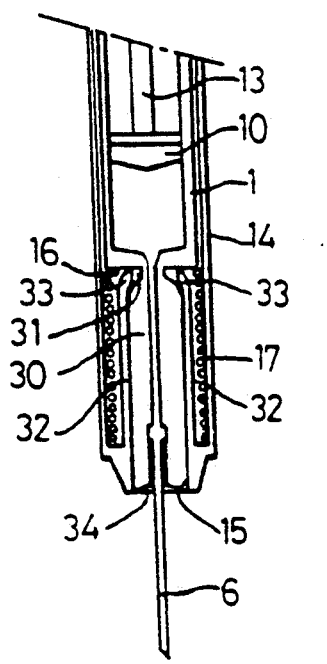
FIG_4
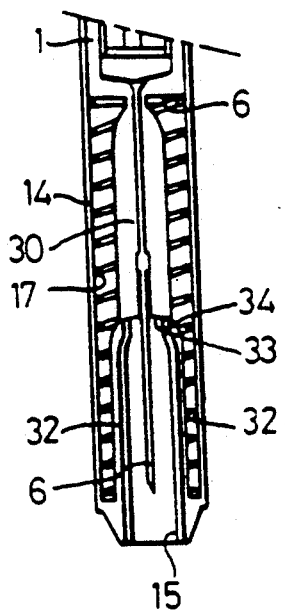
FIG_5
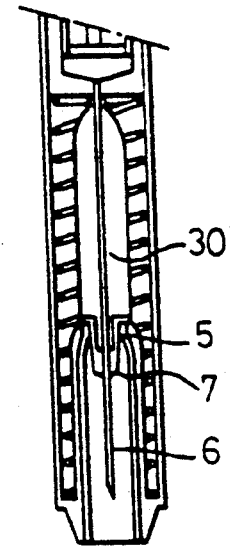
FIG_6
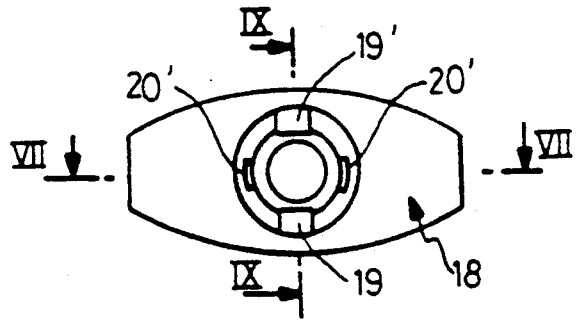
FIG_8
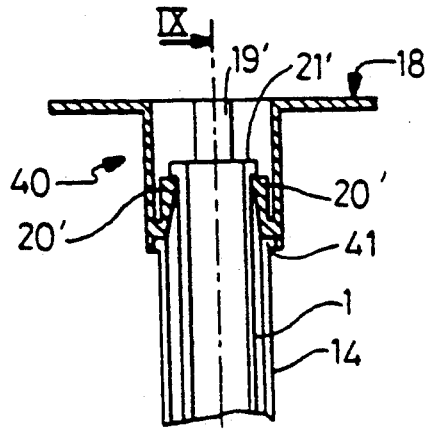
FIG_7
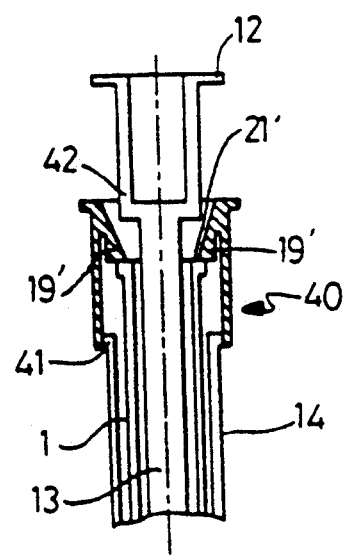
FIG_9

SYRINGE WITH SELF-RETRACTING NEEDLE

This invention relates to medical syringes, i.e. devices serving to inject, by means of a hollow needle, a substance which is usually medicinal, into the body of the patient by intramuscular, hypodermic or intravenous path. This operation is carried out either by a medical functionary or by the patient himself, in which case it is referred to as self-injection.

The utilization of so-called once-only syringes is now generalized. These are sold sterile in a sealed packet and are not to be reused in order to avoid all risks of accidental contamination from one patient to another. However, this very commonplace piece of equipment does not protect medical staff from accidental pricking and does not materially prevent the syringe being reused if the user does not voluntarily destroy it after use.

European patent application No. 0,307,367 describes a syringe with a self-retracting needle, comprising a body carrying at one end a means for supporting an injection needle, a plunger which is mobile within said body, a protective sheath within which said body can slide, and a spring disposed between the sheath and the body. There is also provided a sheath catching means on the body comprising first and second shoulders on the outer wall of the body and at least one flexible toe borne by the sheath so as to cooperate in abutment with the first shoulder for defining a first position of the body in relation to the blocking sheath in a first direction, the spring being compressed and the needle protruding from the sheath in this first position, and with the second shoulder for defining a second blocking position in the same direction, the spring being at least partially released and the needle being withdrawn inside the sheath in this second position. The transition from the first position to the second position is made by cooperation of the plunger with said first flexible toe for freeing the toe of the first shoulder at the end of travel of said plunger, thereby causing the body to retract into the sheath under the effect of the spring until it blocks in the second position.

Such a construction gives partial satisfaction in that, subsequent to injection, the needle is in fact retracted into its sheath. However, this syringe is quite complicated to manufacture, whence a negative impact on its price, and, moreover, is not very reliable. Indeed, the plunger does not cooperate directly with the blocking toes, but through the intermediary of an additional part comprised of an elastic ring, that unscrupulous people can deform to render it usable.

Furthermore, according to the document quoted, the needle is prevented from coming back out by providing a very small sheath hole, just wide enough for the needle which is pre-oriented slantwise to prevent it from coming back out of said hole once it has retracted into the sheath. Such an arrangement has the disadvantage of it being impossible to provide a syringe with interchanging needles since the connection ends of these needles would not be able to get by the sheath hole. In fact, it is often practical for medical staff to be able to adapt a needle of its choosing onto the syringe, e.g. a needle of large diameter to draw liquid into the syringe, and a needle of lesser diameter for injection proper.

The main object of this invention is to provide a new syringe devoid of this disadvantage.

Accordingly, the syringe according to the invention is of the general type, known to the above-mentioned document and recalled above. It differs from the aforesaid in that it comprises at least a second flexible toe and a third shoulder, respectively in the opposite direction to the first flexible toe and two first shoulders, respectively positioned on the sheath and wall of the body for blocking the body in the sheath when it is in the second blocking position, in the opposite direction to the first direction.

In this way, due to this second toe and third shoulder, the blocking of the body in the sheath to prevent the needle from coming back out no longer requires that the sheath exit hole be limited. It is thus possible and desirable, according to the invention, that the lower part of the body be capable of receiving a needle-holding connection end and that the lower end of the sheath comprise a hole for the passage of said connection end.

Advantageously, at least certain and preferably all of the toes are flexible and made all in one piece with the sheath in e.g. a plastic material such as polypropylene, polyethylene or polystyrene. Naturally, the sheath itself can be manufactured in one part or in several assembled parts should this prove simpler.

Very advantageously, at least certain and preferably all of the toes are protected on the outside by a wall in the form of a sleeve interdependent with the sheath, this wall being either mounted onto or comprise a single piece with the sheath. According to one embodiment, this wall is constituted by the sheath itself (or a part of the sheath), the toes being formed inside said sheath.

According to a first embodiment, the toes are comprised by simple cuttings, with possible thickening, from the wall of the sheath, situated opposite one another in slots formed on this wall. The shoulders of the body are advantageously formed by the front sides of substantially square collars or lines disposed by molding in a suitable position of the cylindrical body.

According to a second embodiment, the body comprises a needle-holding chuck, and at least certain toes, notably the second i.e. "reverse-lock" toes, are provided inside the sheath, at its end, to be able to surround said chuck in the first position, and to release it towards the second position and block it there. Advantageously, the needle-holding chuck comprises a less resistant bevelled spot for breakage under undue pressure.

According to a third embodiment, the first and second toes are made inside a mounted sleeve constituting the proximal end of the sheath.

An end of the spring can advantageously be fitted into an area of lesser resistance arranged on the body, where the needle or needle-holding connection end is secured, to enable the needle to separate from the body in the event of attempted re-use.

The plunger comprises a part capable of coming directly into contact with the first blocking toes, at the end of the injection stroke: this part can be constructed in the form of a widening of the plunger rod, or of a skirt on the plunger.

Further features and advantages of the invention will be apparent from the following particular description of several preferred embodiments of this invention as illustrated in the corresponding accompanying drawings in which:

FIG. 1 is a sectional view of a syringe according to a first embodiment of the invention, along line I—I of FIG. 2, in the active position;

FIG. 2 is a side view of the same syringe;

FIG. 3 is a sectional view of the syringe of FIG. 1 after retraction of the body into the sheath;

FIG. 4 is a partial sectional view of the distal end of a second embodiment of the syringe, in the active position;

FIG. 5 is a view similar to that of FIG. 4, in the inactive position;

FIG. 6 is a view similar to that of FIG. 5, with a variation of the needle attachment method;

FIG. 7 is a partial view of the body of the proximal end of a third embodiment of the syringe, along line VII—VII of FIG. 8;

FIG. 8 is a top view of the same embodiment;

FIG. 9 is a sectional view along line IX—IX of FIG. 8.

FIGS. 1 to 3 show a syringe set comprised of a substantially cylindrical body 1 comprising an open end and a partially closed end or bottom 3.

Attached to the bottom 3 is formed a connection end 4, 5 composed of a cylindrical part 4 followed by a tapered part 5 acting as attachment stub for a conventional needle 6 with a tapered mounting piece 7. The connection end 4, 5 is bored with a hole 8 enabling the inside 9 of the body to communicate with the hole of needle 6.

Through the open end 2 of the body 1 can penetrate into the body 1 a plunger 13 with a sealed element 10, a cruciform rod 11 and a thruster 12, sliding freely within the body 1. A peripheral skirt 22 linked to the thruster 22 can cover part of the body 1.

A substantially cylindrical sheath 14 is slidably mounted over the body 1. At one of its ends, its wall narrows to form a hole 15 of sufficient size for the needle mounting stub 5 to pass, and whose contour can act as base to a compressible spring 17 whose other end rests on a shoulder 16 of the body 1, at end 3. When compressed, the spring 17 is maintained around part 4 of the connection end 4, 5 of the body.

The sheath 14 comprises, at its other end, a fingergrip flange 18.

In the wall of the sheath 14 are made two rectangular lateral slots partly formed by two elastically flexible tongues or toes 19 and 20 facing opposite ways.

The first toes 19 cooperate with a first peripheral shoulder 21 formed on the outer wall of the body 1 for performing a first blocking of the body 1 in the sheath 14, in the position of FIGS. 1 or 2 corresponding to activation of the needle, when the spring 17 is compressed. The same toes 19 can be spread apart by the action of the skirt 22 when the plunger 13 is pressed down into the body 1. The spring 17 is then released and moves the sheath 14 apart from the body 1 until the second blocking position is reached in which the toes 19 cooperate with a second peripheral shoulder 23 (position shown in FIG. 3) situated at the base of the body 1.

The toes 19 and the shoulder 23 thus prevent the body 1 and its needle 6 from being pulled out of the sheath 14 which then covers it.

The second toes 20, acting in the opposite direction to the toes 19, are intended to prohibit a further exiting of the needle 6 from the sheath 14, exiting that the mere width of the hole 15 is not enough to prevent. To achieve this, the toes 20 cooperate with a third shoulder 24 (facing the opposite way to shoulders 31 and 23), e.g. comprised of the edge of the rest shoulder 16 of spring 17. In this manner, after the injection, the body 1 remains blocked, at the rear and at the front, in the position represented in FIG. 3 and the needle 6 is inaccessible. Naturally, the plunger 13, which is completely conventional, can be removed from the body 1 (it has not been represented in FIG. 3).

Toes 19 and 20 are preferably constructed in the form of flexible tongues having a certain additional thickness forming on the inside of the sheath a one-way blocking protrusion in one direction and a ramp in the other direction and being aligned, in their normal state, with the outer cylindrical wall of the sheath 14. In this way, it is hard to access them from the outside, thereby avoiding all accidental handling on the part of medical staff. Naturally, the toes 20 must be capable of being moved apart temporarily from the outside by the assembly machine for installing the syringe in the active position of FIG. 1, in order to let shoulder 24 pass, as well as any other shoulder facing in the same direction, such as e.g. shoulder 25 shown in FIG. 1, situated on the outer wall of the body 1 along the downward stroke of the body into the sheath below the level of the toes 20.

In the case of use planned by individuals tempted to reuse the syringe by all means after a first injection, it is possible to add, at the end of assembly, a protection ring 26 secured by glueing, welding or otherwise to the sheath 14 for covering the toes 19 and 20 and thus rendering them totally inaccessible, while nevertheless enabling them to freely fulfill their role and move apart at the required moment: toes 19 upon deactivation at the end of the stroke of the plunger 13 into the syringe, and toes 20 upon retraction of the body into the sheath after deactivation.

This protection ring 26 is preferably air-tight, in such a way that by fitting the sheath with a protection cap 27 (FIG. 3), also air-tight, the assembled syringe can be sterilized without individual packaging, as is the case with certain insulin syringes.

It should be noted that a recess 27 has been advantageously provided on the body to enable toes 20 to be at rest like toes 19 (i.e. they are not subjected to any constraint) when the syringe is in the active position. The integrity and the elastic qualities of the two opposing toes are thus preserved throughout storage of the assembled syringe.

The second embodiment illustrated in FIGS. 4 to 6 differs mainly from the first by the realization of second reverse-lock blocking toes.

In this embodiment we again have the body 1 and the inner plunger 13 with sliding tightness 10, and an outer sliding sheath 14 and a spring 17 maintained between the end of the sheath 14 and a shoulder 16 to the front of the body 1.

The body is further prolonged at the front by a substantially cylindrical bored needle-holding chuck 30, of length equal to that of the needle 6 plus a few millimeters, and presenting a narrowing 31 at its base, on the syringe side.

The sheath 14 has at its ends six flexible axial tabs 32 spread circumferentially around the hole 15 and fitted at their inner ends with a toe 33 pointed radially inwards.

Prior to utilization, the body 1 of the syringe is presented fully pressed into the sheath 14 (FIG. 4): the needle-holding chuck 30 then becomes flush with the edge of the hole, while the tabs surround said chuck and are at rest since their protruding toes 33 are housed without difficulty at the level of the bevelled part 31. The spring 17 is coiled: the syringe is active.

The operation of the syringe is identical to that of the first embodiment as regards deactivation. However, during the ensuing retraction of the body 1 into the sheath 14, the flexible tabs 32 move apart around the chuck 30 because of the toes 33 and the, thanks to their elasticity, reposition themselves at the end of their stroke (FIG. 5) so as to block the body 1 of the syringe against the shoulder 34 formed by the end of the chuck 30 resting against the toes 33. The shoulder 34 and the toes 33 are formed in complementary concave-convex manner in order that any increase of the thrust should reinforce the blocking action. Moreover, if the thruster is forced, the bevelled part 31, which is more fragile, can break in order to radically eliminate all possibilities of re-use.

While a fixed glued needle was represented in FIGS. 4 and 5, it is perfectly possible, with the same embodiment, to end the needle-holding chuck 30 by an attachment stub 5 for an interchangeable needle 6 carrying its own attachment connection end 7 (FIG. 6).

The syringe assembly machine must comprise a device to temporarily move the tabs 32 apart for affording an initial passage for the chuck 30.

It should be noted that even in the embodiment of FIGS. 1 to 3, a fringeable bevelled part, similar to that of the chuck 30, can be provided at the base of the connection end 4, 5. In this case, advantage is taken of this narrowing to firmly lodge the last spiral of the spring 17 there. In this way, even if the sheath has been successfully cut open to recuperate the syringe and its needle, any attempt to dislodge the spring 17 from its bevelled area of lesser resistance will cause breakage and therefore separation of the connection end 4, 5 from the body of the syringe. Re-utilization of the needle and/or syringe will become impossible.

According to the embodiment in FIGS. 7 to 9, toes 19 and 20 are replaced by toes 19' and 20' borne by a substantially cylindrical sleeve made interdependent with the sheath 14 by all suitable means such as glueing, ultrasonic sealing, heat fusing, etc. of an edge 41 of the sheath 14 in a groove of the sleeve 40. The sleeve 40 in turn bears the gripping flange 18.

Toes 19' and 20' are provided inside said sleeve 40 and can be made all in one piece with the latter, e.g. by molding. The two toes 19' are pointed towards the base and can come and cooperate with the shoulder 21' of the body 1 formed by its upper edge for the active position, or with a second shoulder not represented situated lower down on the body 1 for the inactive position. Deactivation is triggered by the cooperation of a bulge 42 provided at the rear of the plunger rod 13 and is intended, on the one hand, for moving toes 19' apart at the end of the stroke, and on the other hand, for resting on the edge 21'.

Toes 20' are positioned in quadrature with and in opposite direction to toes 19' for cooperating, after retraction of the syringe body, with a suitable reverse-locking shoulder positioned on the body 1.

This embodiment has major advantages as regards assembly and security. In fact, during assembly, no temporary device is required for moving the toes apart, it being sufficient to completely fit the body 1 into the sheath 14, to cover this assembly with the sleeve 40 which is then attached, and to fit the plunger into position.

The body 1 adapted to this embodiment can be of particularly simple form, e.g. a cylindrical form bearing at or near its proximal end a flange or line forming the edge 21' of the first shoulder, and further on its body or from the distal end, a peripheral line forming the second shoulder on one side and the third shoulder on the other side.

We claim:

1. A syringe with a self-retracting needle, comprising a body (1) carrying at one end a means (5) for supporting an injection needle (6), a plunger (13) which is movable within said body, a protective sheath (14) within which said body (1) can slide, a spring (17) disposed between said sheath (14) and said body (1), a means for catching said sheath (14) on the body (1) comprising first and second shoulders (21, 23) on the outer wall of said body (1) and at least a first flexible toe (19) borne by said sheath (14) so as to cooperate in abutment with said first shoulder (21) for defining a first blocking position of said body (1) in relation to said sheath (14) in a first direction, said spring (17) being compressed and said needle (6) protruding from said sheath in this first position, and with said second shoulder (23) for defining a second blocking position in the same direction, said spring (17) being at least partially released and said needle (6) being withdrawn inside said sheath (14) in this second position, the transition from said first position to said second position being made by cooperation of said plunger (13) with said first flexible toe (19) for freeing said toe (19) of said first shoulder (21) at the end of stroke of said plunger (13), thereby causing said body (1) to retract into said sheath (14) under the effect of said spring (17) until it blocks in said second position, characterized in that it comprises at least a second flexible toe (20, 20', 33) and a third shoulder (24), respectively in the opposite direction to said first flexible toe (19) and two first shoulders (21, 23), respectively positioned on said sheath (14) and wall of said body (1) for blocking said body (1) in said sheath (14) when it is in said second blocking position, in the opposite direction to said first direction.

2. The syringe as claimed in claim 1, characterized in that the lower part (5) of said body (1) is arranged for receiving a needle-holding connection end (7) and the bottom end of said sheath comprises a hole (15) for the passage of said connection end.

3. The syringe as claimed in claim 1, characterized in that at least certain toes (15, 19) are flexible and made integral with said sheath (14).

4. The syringe as claimed in claim 1, characterized in that at least certain toes (15, 19) are protected on the outside by a wall in the form of a sleeve (26, 40) fixed with said sheath.

5. The syringe as claimed in claim 1, characterized in that said body (1) comprises a needle-holding chuck (30) and at least certain of said toes (33) are provided inside said sheath (14) and around said chuck.

6. The syringe as claimed in claim 1, characterized in that said needle-holding chuck (30) comprises a restricted portion (31).

7. The syringe as claimed in claim 1, characterized in that an end of said spring (17) is lodged in an area of lesser resistance provided on said body (1).

8. The syringe as claimed in claim 1, characterized in that said syringe plunger (13) comprises a part (22, 42) arranged for directly engaging with said first toes (19).

9. The syringe as claimed in claim 2 characterized in that at least certain toes (15, 19) are flexible and made integral with said sheath (14).

10. The syringe as claimed in claim 9 characterized in that at least certain toes (15, 19) are protected on the outside by a wall in the form of a sleeve (26, 40) fixed with said sheath.

11. The syringe as claimed in claim 10, characterized in that said body (1) comprises a needle-holding chuck

(30) and at least certain of said toes (33) are provided inside said sheath (14) and around said chuck.

12. The syringe as claimed in claim 11, characterized in that said needle-holding chuck (30) comprises a restricted portion (31).

13. The syringe as claimed in claim 12, characterized in that an end of said spring (17) is lodged in an area of lesser resistance provided on said body (1).

14. The syringe as claimed in claim 13, characterized in that said syringe plunger (13) comprises a part (22, 42) arranged for directly engaging with said first toes (19).

* * * * *